(12) United States Patent
Hosokawa et al.

(10) Patent No.: US 7,834,346 B2
(45) Date of Patent: Nov. 16, 2010

(54) NITROGENOUS HETEROCYCLIC DERIVATIVE AND ORGANIC ELECTROLUMINESCENCE DEVICE MAKING USE OF THE SAME

(75) Inventors: Chishio Hosokawa, Chiba (JP); Hiroshi Yamamoto, Chiba (JP); Takashi Arakane, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 431 days.

(21) Appl. No.: 11/997,919

(22) PCT Filed: Jul. 6, 2006

(86) PCT No.: PCT/JP2006/313469

§ 371 (c)(1),
(2), (4) Date: Feb. 5, 2008

(87) PCT Pub. No.: WO2007/018004

PCT Pub. Date: Feb. 15, 2007

(65) Prior Publication Data

US 2010/0108990 A1      May 6, 2010

(30) Foreign Application Priority Data

Aug. 5, 2005   (JP) .............................. 2005-227614

(51) Int. Cl.
*H01L 29/227* (2006.01)
(52) U.S. Cl. ................................. 257/40; 257/E51.028
(58) Field of Classification Search .................. 257/40, 257/E29.296, E51.028; 313/504
See application file for complete search history.

(56) References Cited

U.S. PATENT DOCUMENTS

| 7,238,437 | B2 * | 7/2007 | Igarashi et al. | 428/690 |
| 7,501,189 | B2 * | 3/2009 | Tokailin et al. | 428/690 |
| 7,579,093 | B2 * | 8/2009 | Sano et al. | 428/690 |
| 2001/0012572 | A1 * | 8/2001 | Araki | 428/690 |
| 2005/0072970 | A1 * | 4/2005 | Saito | 257/40 |
| 2005/0191519 | A1 * | 9/2005 | Mishima et al. | 428/690 |

FOREIGN PATENT DOCUMENTS

| JP | 05 331459 | 12/1993 |
| JP | 2001 267080 | 9/2001 |
| JP | 2004 175691 | 6/2004 |
| JP | 3562652 | 9/2004 |
| JP | 2004 277377 | 10/2004 |
| JP | 2005 108720 | 4/2005 |

* cited by examiner

*Primary Examiner*—Nathan W Ha
(74) *Attorney, Agent, or Firm*—Oblon, Spivak, McClelland, Maier & Neustadt, L.L.P.

(57) ABSTRACT

Provided are a nitrogen-containing heterocyclic derivative having a specific structure and an organic electroluminescence device in which an organic thin film layer comprising a single layer or plural layers including at least a light emitting layer is interposed between a cathode and an anode, wherein at least one layer in the above organic thin film layer contains the nitrogen-containing heterocyclic derivative described above in the form of a single component or a mixed component, and thus provided are the organic electroluminescence device which emits blue light having a high light emitting luminance and a high current efficiency and the novel nitrogen-containing heterocyclic derivative which materializes the same.

10 Claims, No Drawings

NITROGENOUS HETEROCYCLIC DERIVATIVE AND ORGANIC ELECTROLUMINESCENCE DEVICE MAKING USE OF THE SAME

BACKGROUND OF THE INVENTION

The present invention relates to a novel nitrogen-containing heterocyclic derivative, a material for an organic electroluminescence (EL) device obtained by using the same and an organic electroluminescence device comprising the same, specifically to a nitrogen-containing heterocyclic derivative which is useful as a constitutional component for an organic EL device, a material for an organic EL device obtained by using the same and an organic electroluminescence device which is enhanced in a light emitting luminance and a current efficiency while operated at a low voltage by using the above nitrogen-containing heterocyclic derivative for at least one layer in an organic compound layer.

RELATED ART

An organic electroluminescence (EL) device obtained by using organic materials is assumed to be promising in uses of an inexpensive large area full color display device of a solid light emitting type, and a lot of developments therefor has been carried out. In general, an EL device is constituted from a light emitting layer and a pair of counter electrodes provided so that they interpose the above layer. Light emission is a phenomenon in which when an electric field is applied between both electrodes, electrons are injected from a cathode side, and holes are injected from an anode side; further, the above electrons are recombined with the holes in a light emitting layer to form an excited state, and energy is discharged in the form of light when the excited state goes back to the ground state.

Conventional organic EL devices have been kept high in an operating voltage and low in a light emitting luminance and a current efficiency as compared with inorganic light emitting diodes. Further, they are notably deteriorated in characteristics and therefore have not come to be put to practical use. In recent years, organic EL devices are gradually improved but required to show a high light emitting luminance and a high current efficiency at low voltage.

In order to solve the above problems, a specific phenanthroline derivative is used for an electron transporting material in, for example, a patent document 1 and shows a high current efficiency, but involved therein are the problems that it is crystallized by applying current for a long time and that it has a markedly short durability. Further, a compound having a benzimidazole ring and an anthracene skeleton is described in a patent document 2. However, required are organic EL devices which are improved more in a light emitting luminance and a current efficiency than organic EL devices prepared by using the above compounds.

Patent document 1: Japanese Patent No. 3562652

Patent document 2: Japanese Patent Application Laid-Open No. 267080/2001

DISCLOSURE OF THE INVENTION

The present invention has been made in order to solve the problems described above, and an object thereof is to provide a novel nitrogen-containing heterocyclic derivative which is useful as a constitutional component for an organic EL device and materialize an organic EL device which is enhanced in a light emitting luminance and a current efficiency while operated at a low voltage by using the above nitrogen-containing heterocyclic derivative for at least one layer in an organic compound layer.

Intensive researches repeated by the present inventors in order to achieve the object described above have resulted in finding that a reduction in an operating voltage and an increase in a light emitting luminance and a current efficiency in an organic EL device can be achieved by using a novel nitrogen-containing heterocyclic derivative having a specific structure for at least one layer in an organic compound layer of the organic EL device, and thus the present inventors have come to complete the present invention.

That is, the present invention provides a nitrogen-containing heterocyclic derivative represented by the following Formula (1):

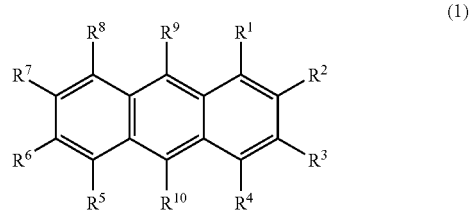

(1)

in Formula (1), $R^1$ to $R^{10}$ are a hydrogen atom, a substituted or non-substituted aryl group having 5 to 60 ring atoms, a pyridyl group which may have a substituent, a quinolyl group which may have a substituent, a substituted or non-substituted alkyl group having 1 to 50 carbon atoms, a substituted or non-substituted cycloalkyl group having 3 to 50 carbon atoms, a substituted or non-substituted aralkyl group having 6 to 50 ring atoms, a substituted or non-substituted alkoxy group having 1 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group; a pair of the adjacent substituents in $R^1$ to $R^{10}$ may be combined with each other to form an aromatic ring; and at least one of $R^1$ to $R^{10}$ is a substituent represented by Formula (2):

(2)

in Formula (2), L is an arylene group having 6 to 60 carbon atoms which may have a substituent, a pyridinylene group which may have a substituent, a quinolinylene group which may have a substituent or a fluorenylene group which may have a substituent; and HAr is a substituent formed by removing any one of $R^{1a}$ to $R^{8a}$ in a structure represented by the following Formula (3):

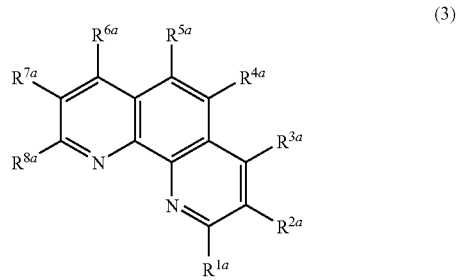

(3)

in Formula (3), $R^{1a}$ to $R^{8a}$ are a hydrogen atom, a substituted or non-substituted aryl group having 5 to 60 ring atoms, a pyridyl group which may have a substituent, a quinolyl group which may have a substituent, a substituted or non-substituted alkyl group having 1 to 50 carbon atoms, a substituted or non-substituted cycloalkyl group having 3 to 50 carbon atoms, a substituted or non-substituted aralkyl group having 6 to 50 ring atoms, a substituted or non-substituted alkoxy group having 1 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group; and a pair of the adjacent substituents in $R^1$ to $R^{10}$ may be combined with each other to form an aromatic ring.

Further, the present invention provides an organic EL device in which an organic thin film layer comprising a single layer or plural layers comprising at least a light emitting layer is interposed between a cathode and an anode, wherein at least one layer in the above organic thin film layer contains the nitrogen-containing heterocyclic derivative described above in the form of a single component or a mixed component.

In the organic EL device, at least one layer in the organic thin film layer contains the nitrogen-containing heterocyclic derivative of the present invention represented by Formula (1) described above in the form of a single component or a mixed component, whereby the organic EL device which has a high current efficiency and is excellent in an electron transporting property while operated at a low voltage can be prepared.

The nitrogen-containing heterocyclic derivative of the present invention is represented by the following Formula (1):

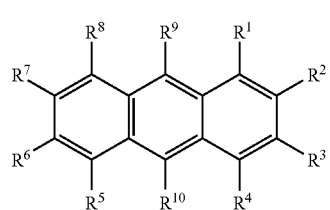

(1)

in Formula (1), $R^1$ to $R^{10}$ are a hydrogen atom, a substituted or non-substituted aryl group having 5 to 60 ring atoms, a pyridyl group which may have a substituent, a quinolyl group which may have a substituent, a substituted or non-substituted alkyl group having 1 to 50 carbon atoms, a substituted or non-substituted cycloalkyl group having 3 to 50 carbon atoms, a substituted or non-substituted aralkyl group having 6 to 50 ring atoms, a substituted or non-substituted alkoxy group having 1 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group; a pair of the adjacent substituents in $R^1$ to $R^{10}$ may be combined with each other to form an aromatic ring; and at least one of $R^1$ to $R^{10}$ is a substituent represented by Formula (2):

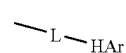

(2)

in Formula (2), L is an arylene group having 6 to 60 carbon atoms which may have a substituent, a pyridinylene group which may have a substituent, a quinolinylene group which may have a substituent or a fluorenylene group which may have a substituent; and HAr is a substituent formed by removing any one of $R^{1a}$ to $R^{8a}$ in a structure represented by the following Formula (3):

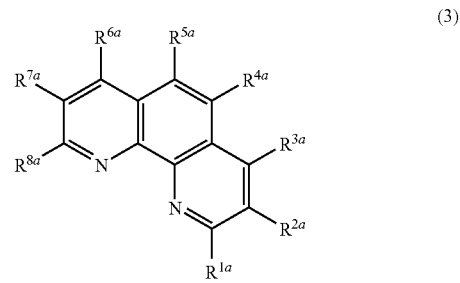

(3)

in Formula (3), $R^{1a}$ to $R^{8a}$ are a hydrogen atom, a substituted or non-substituted aryl group having 5 to 60 ring atoms, a pyridyl group which may have a substituent, a quinolyl group which may have a substituent, a substituted or non-substituted alkyl group having 1 to 50 carbon atoms, a substituted or non-substituted cycloalkyl group having 3 to 50 carbon atoms, a substituted or non-substituted aralkyl group having 6 to 50 ring atoms, a substituted or non-substituted alkoxy group having 1 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group; and a pair of the adjacent substituents in $R^{1a}$ to $R^{8a}$ may be combined with each other to form an aromatic ring.

The nitrogen-containing heterocyclic derivative of the present invention is represented by the following Formula (1-a), (1-b), (1-c) or (1-d):

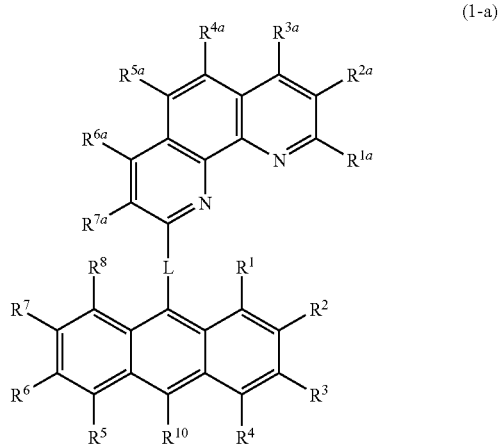

(1-a)

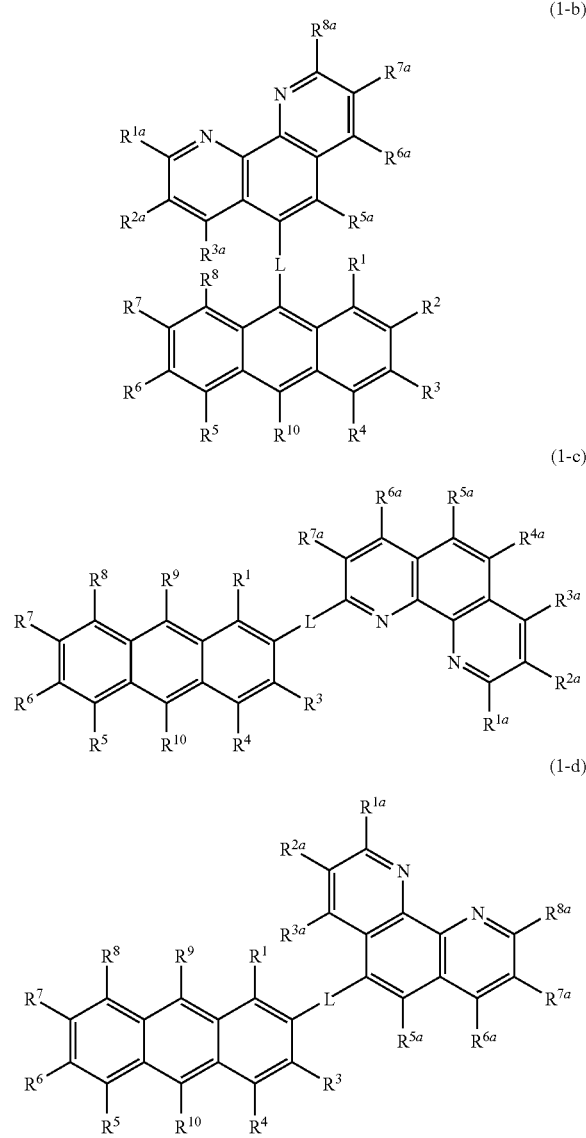

in Formulas (1-a) to (1-d), $R^1$ to $R^{10}$ are the same as the groups in Formula (1); $R^{1a}$ to $R^{8a}$ are the same as the groups in Formula (3); and L is the same as the group in Formula (2).

Further, in the organic EL device of the present invention, an organic thin film layer comprising a single layer or plural layers comprising at least a light emitting layer is interposed between a cathode and an anode, and at least one layer in the above organic thin film layer contains the nitrogen-containing heterocyclic derivative of the present invention described above in the form of a single component or a mixed component.

The substituted or non-substituted aryl group having 5 to 60 ring carbon atoms and the heterocyclic group which are represented by $R^1$ to $R^{10}$ and $R^{1a}$ to $R^{8a}$ include, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

Among them, preferred are phenyl, naphthyl, biphenyl, anthranyl, phenanthryl, pyrenyl, chrysenyl, fluoranthenyl and fluorenyl.

The substituted or non-substituted alkyl group having 1 to 50 ring carbon atoms represented by $R^1$ to $R^{10}$ and $R^{1a}$ to $R^{8a}$ includes methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The specific examples of the substituted or non-substituted cycloalkyl group having 3 to 50 carbon atoms represented by $R^1$ to $R^{10}$ and $R^{1a}$ to $R^{8a}$ include, for example, cyclopropyl, cyclobutyl, cyclopentyl, cyclohexyl, 4-methylcyclohexyl, 1-adamantyl, 2-adamantyl, 1-norbornyl, 2-norbornyl and the like.

The examples of the substituted or non-substituted aralkyl group having 6 to 50 ring carbon atoms represented by $R^1$ to $R^{10}$ and $R^{1a}$ to $R^{8a}$ include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, 3-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

The substituted or non-substituted alkoxy group having 1 to 50 carbon atoms represented by $R^1$ to $R^{10}$ and $R^{1a}$ to $R^{8a}$ is a group represented by —OY, and the examples of Y include the same examples as explained in the alkyl group described above.

The substituted or non-substituted aryloxy group having 5 to 50 ring atoms represented by $R^1$ to $R^{10}$ and $R^{1a}$ to $R^{8a}$ is represented by —OY', and the examples of Y' include the same examples as explained in the aryl group described above.

The substituted or non-substituted arylthio group having 5 to 50 ring atoms represented by $R^1$ to $R^{10}$ and $R^{1a}$ to $R^{8a}$ is represented by —SY', and the examples of Y' include the same examples as explained in the aryl group described above.

The substituted or non-substituted alkoxycarbonyl group having 1 to 50 carbon atoms represented by $R^1$ to $R^{10}$ and $R^{1a}$ to $R^{8a}$ is a group represented by —COOY, and the examples of Y include the same examples as explained in the alkyl group described above.

The examples of the aryl group in the amino group substituted with the substituted or non-substituted aryl group having 5 to 50 ring atoms represented by $R^1$ to $R^{10}$ and $R^{1a}$ to $R^{8a}$ include the same examples as explained in the aryl group described above.

The halogen atom represented by $R^1$ to $R^{10}$ and $R^{1a}$ to $R^{8a}$ includes a fluorine atom, a chlorine atom, a bromine atom and an iodine atom.

A pair of adjacent substituents in $R^1$ to $R^{10}$ and $R^{1a}$ to $R^{8a}$ may be combined with each other to form an aromatic ring, and the ring formed is preferably a five-membered ring or a six-membered ring, particularly preferably a six-membered ring.

The arylene group having 6 to 60 carbon atoms in L of Formula (2) is a divalent substituent which can be formed by removing further one hydrogen atom from the substituent explained in the aryl group represented by $R^1$ to $R^{10}$, and it is preferably phenylene, naphthylene, biphenylene, anthranylene, phenanthrylene, pyrenylene, chrysenylene, fluoranthenylene or fluorenylene.

The nitrogen-containing heterocyclic derivative of the present invention is preferably a material for an organic EL device, more preferably a light emitting material for an organic EL device, an electron injecting material for an organic EL device or an electron transporting material for an organic EL device.

The specific examples of the nitrogen-containing heterocyclic derivative of the present invention represented by Formula (1) are shown below, but they shall not be restricted to these compounds shown as the examples.

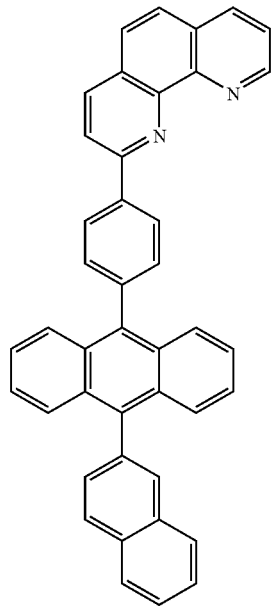

-continued
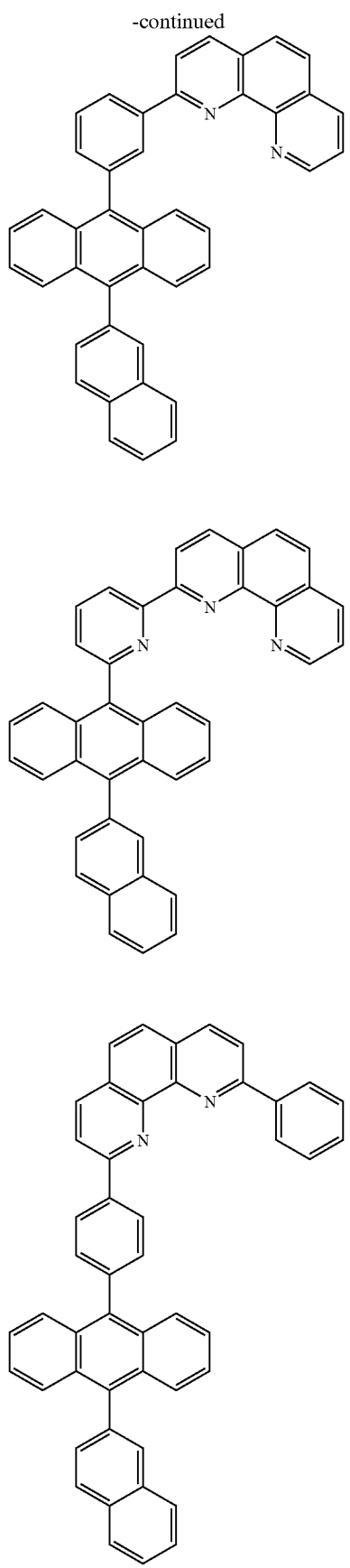

-continued
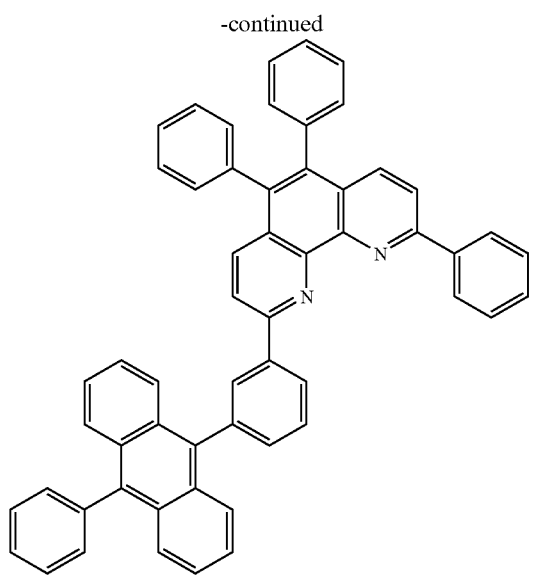
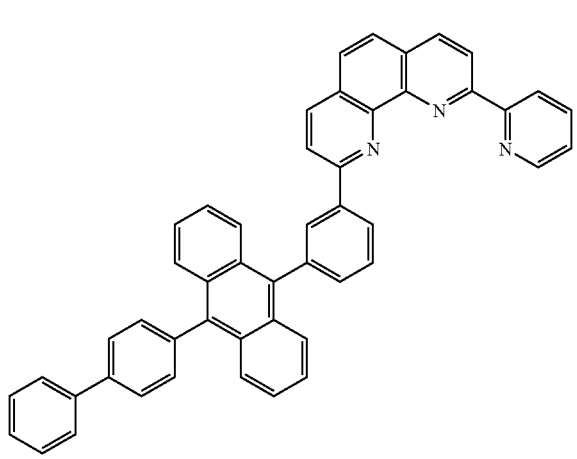
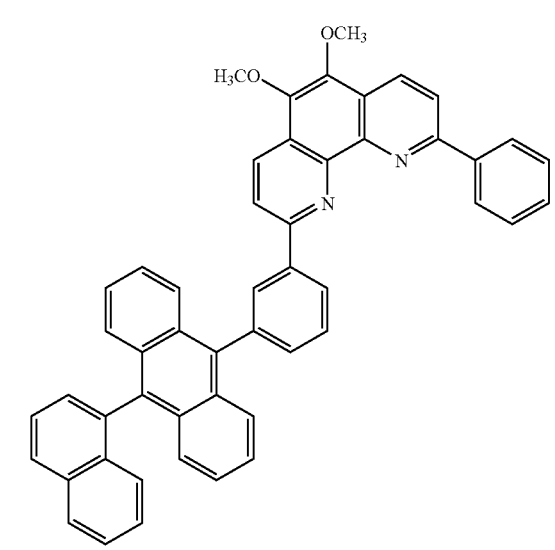
-continued
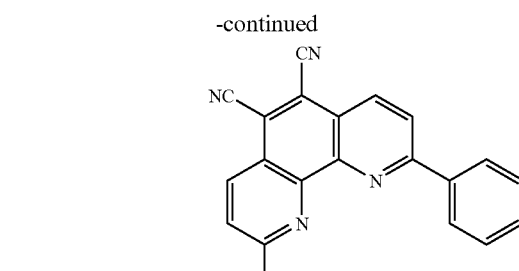
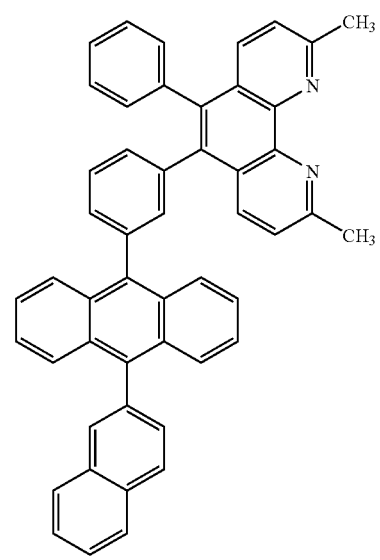
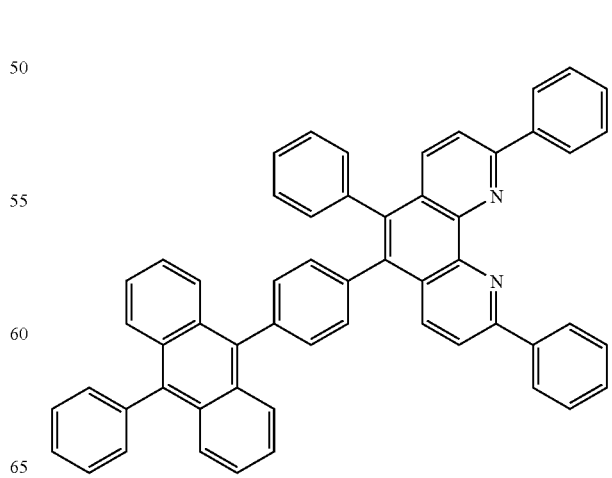

-continued
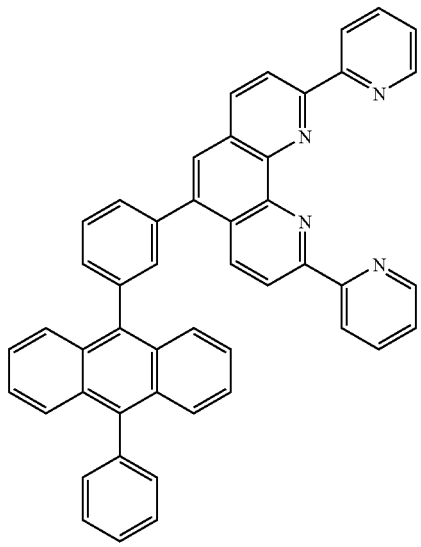
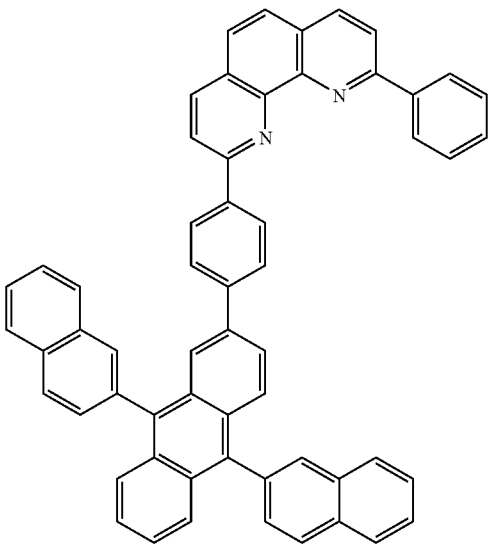
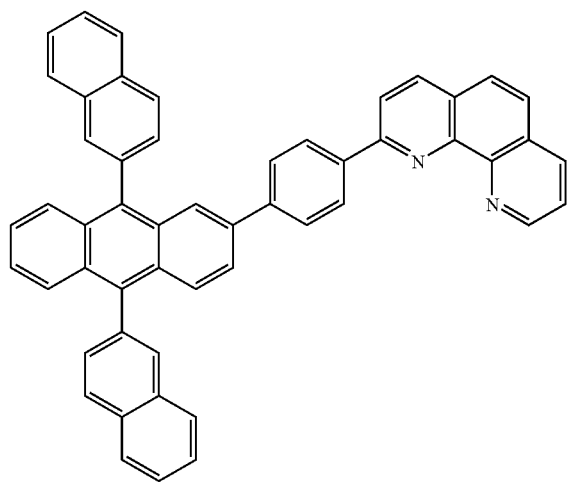
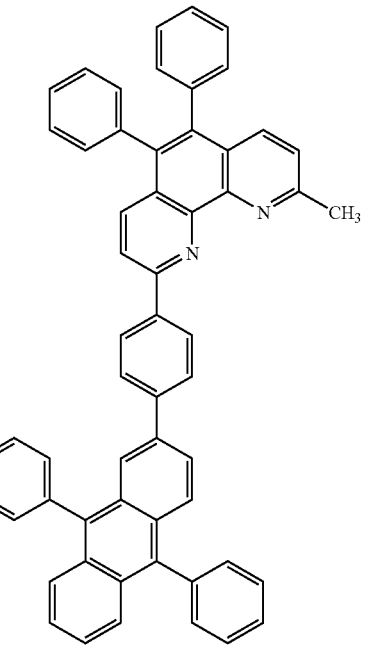

-continued
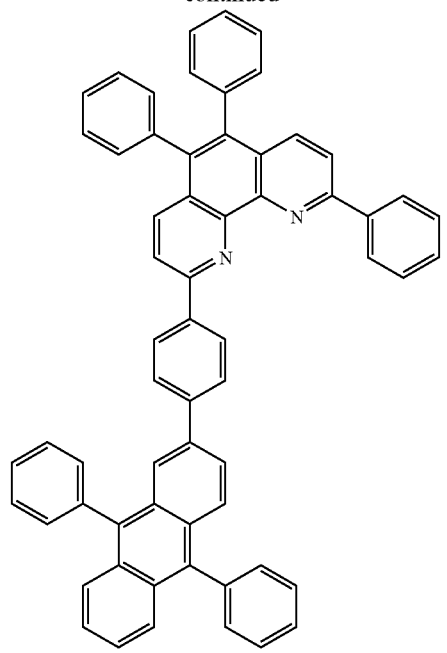
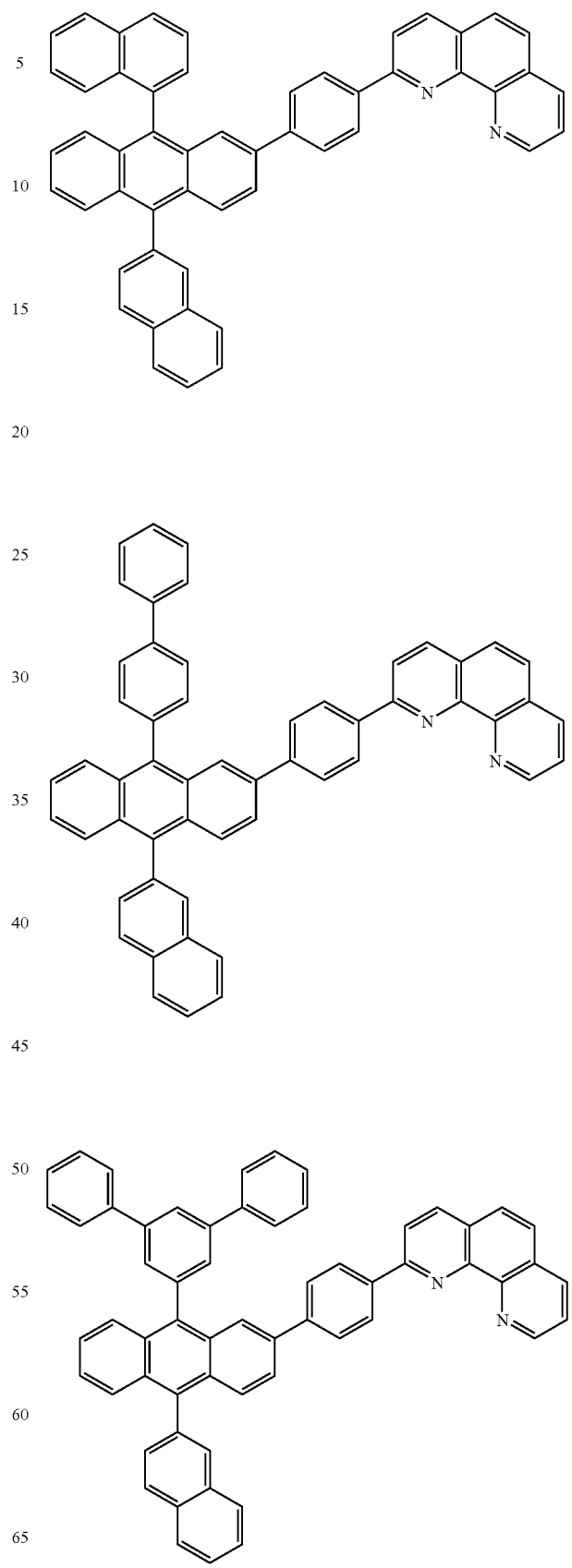

-continued
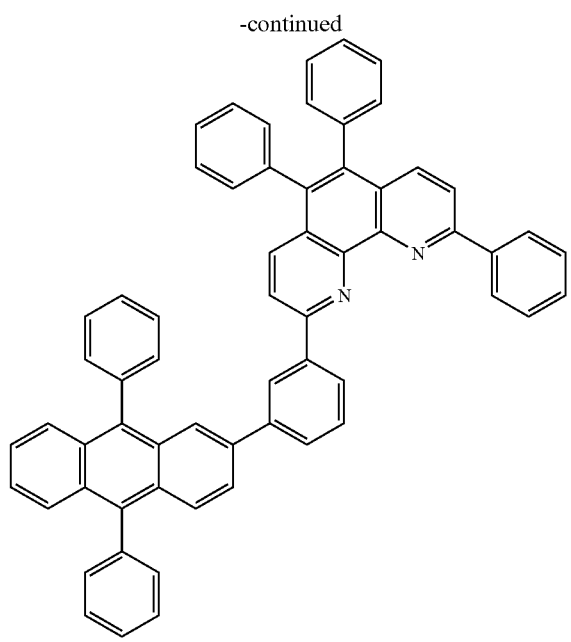
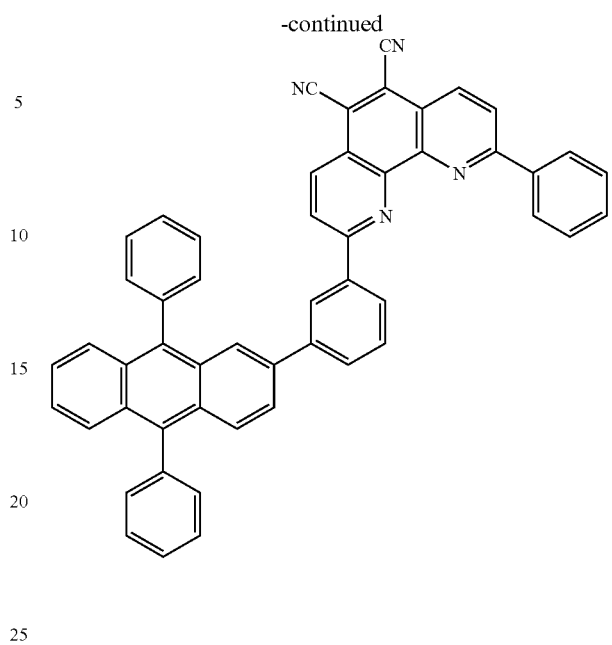
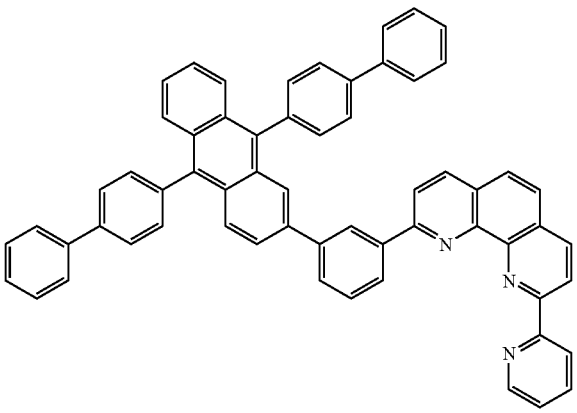
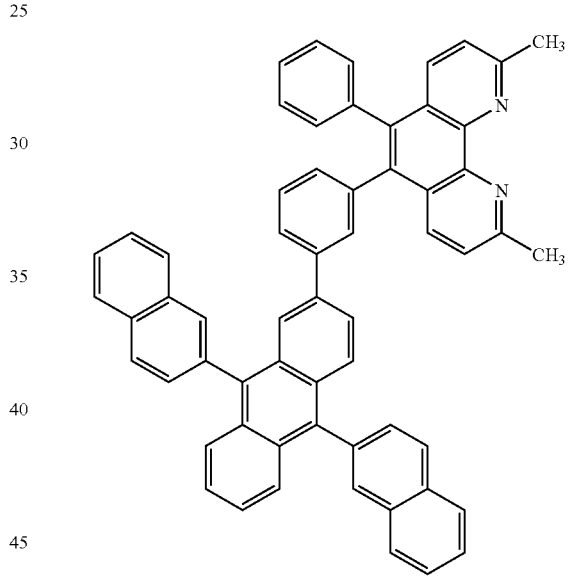
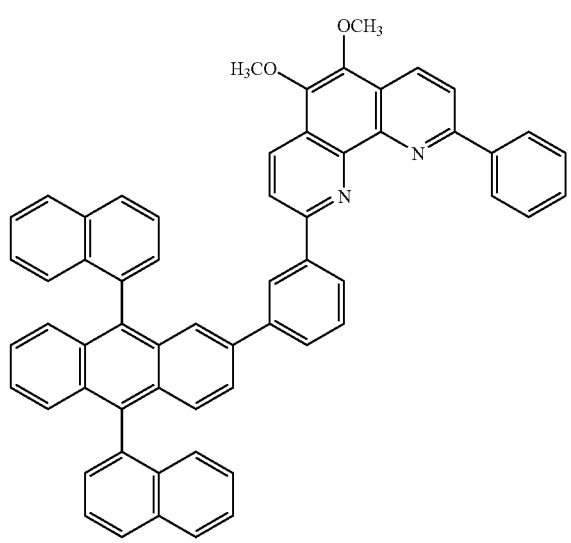
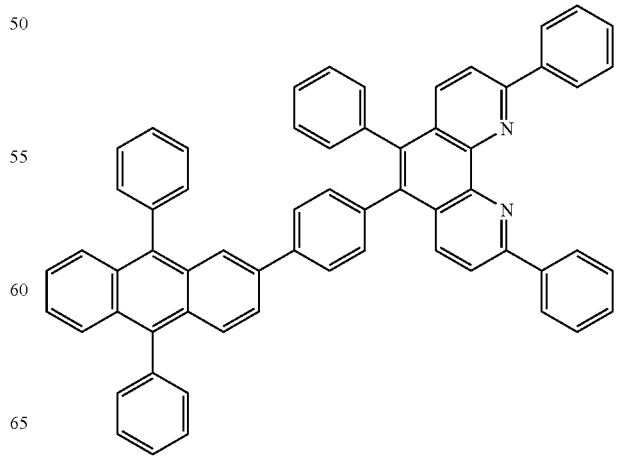

-continued

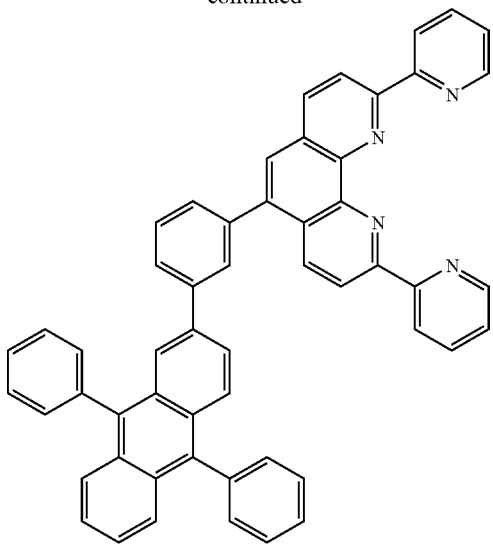

Next, the organic EL device of the present invention shall be explained.

In the organic EL device of the present invention in which an organic thin film layer comprising a single layer or plural layers including at least a light emitting layer is interposed between a cathode and an anode, at least one layer in the above organic thin film layer contains the nitrogen-containing heterocyclic derivative described above in the form of a single component or a mixed component.

In the organic EL device of the present invention, the organic thin film layer described above comprises an electron injecting layer or an electron transporting layer, and the above electron injecting layer or electron transporting layer contains preferably the nitrogen-containing heterocyclic derivative of the present invention in the form of a single component or a mixed component. Further, the light emitting layer described above contains more preferably the nitrogen-containing heterocyclic derivative in the form of a single component or a mixed component.

The device constitution of the organic EL device of the present invention shall be explained below.

(1) Constitution of the Organic EL Device

The representative device constitution of the organic EL device of the present invention includes constitutions such as:
(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/electron injecting layer/cathode
(9) anode/insulating layer/light emitting layer/insulating layer/cathode,
(10) anode/inorganic semiconductor layer/insulating layer/light emitting layer/insulating layer/cathode
(11) anode/organic semiconductor layer/insulating layer/light emitting layer/insulating layer/cathode,
(12) anode/insulating layer/hole injecting layer/hole transporting layer/light emitting layer/insulating layer/cathode and
(13) anode/insulating layer/hole injecting layer/hole transporting layer/light emitting layer/electron injecting layer/cathode Among them, usually the constitution of (8) is preferably used, but the device constitution shall not be restricted to them.

The nitrogen-containing heterocyclic derivative of the present invention may be used in any organic thin film layers of the organic EL device and can be used preferably in the light emitting zone or the hole transporting zone, and it is used particularly preferably in the electron injecting layer, the electron transporting layer or the light emitting layer.

(2) Light Transmitting Substrate

The organic EL device of the present invention is prepared on a light transmitting substrate. The light transmitting substrate referred to in this case is a substrate for supporting the organic EL device, and it is preferably a flat substrate in which light in a visible region of 400 to 700 nm has a transmittance of 50% or more.

To be specific, it includes a glass plate, a polymer plate and the like. In particular, the glass plate includes soda lime glass, barium.strontium-containing glass, lead glass, aluminosilicate glass, borosilicate glass, barium borosilicate glass, quartz and the like. The polymer plate includes polycarbonate, acryl, polyethylene terephthalate, polyether sulfide, polysulfone and the like.

(3) Anode

An anode in the organic EL device of the present invention has a function of injecting a hole into the hole transporting layer or the light emitting layer, and it is effective to provide the anode with a work function of 4.5 eV or more. The specific examples of a material for the anode used in the present invention include indium tin oxide alloy (ITO), tin oxide (NESA), indium-zinc oxide (IZO), gold, silver, platinum, copper and the like.

The anode can be prepared by forming a thin film from the above electrode substances by a method such as a vapor deposition method, a sputtering method and the like.

When light emitted from the light emitting layer is taken out from the anode, a transmittance of light in the anode based on light emitted is preferably larger than 10%. A sheet resistance of the anode is preferably several hundred Ω/square or less. A film thickness of the anode is selected, though depending on the material, in a range of usually 10 nm to 1 μm, preferably 10 to 200 nm.

(4) Light Emitting Layer

The light emitting layer in the organic EL device has the following functions of (1) to (3) in combination.

(1) injecting function: a function in which a hole can be injected from an anode or a hole injecting layer in applying an electric field and in which an electron can be injected from a cathode or an electron injecting layer, (2) transporting function: a function in which a charge (electron and hole) injected is transferred by virtue of a force of an electric field and (3) light emitting function: a function in which a field for recombination of an electron and a hole is provided and in which this is connected to light emission. Provided that a difference may be present between the hole injection efficiency and the electron injection efficiency, and that a difference may be present in a transporting ability shown by the mobilities of a hole and an electron, and any one of the charges is preferably transferred.

A publicly known method such as, for example, a vapor deposition method, a spin coating method, an LB method and the like can be applied as a method for forming the above light emitting layer. In particular, the light emitting layer is preferably a molecular deposit film. In this regard, the molecular deposit film means a thin film formed by depositing a material compound staying in a gas phase state and a film formed by solidifying a material compound staying in a solution state or a liquid phase state, and the above molecular deposit film can usually be distinguished from a thin film (molecular accumulation film) formed by an LB method by a difference in an aggregation structure and a higher order structure and a functional difference originating in it.

Further, as disclosed in Japanese Patent Application Laid-Open No. 51781/1982, the light emitting layer can be formed as well by dissolving a binding agent such as a resin and the material compound in a solvent to prepare a solution and then forming a thin film by a spin coating method and the like.

In the present invention, other publicly known light emitting materials excluding the light emitting material comprising the nitrogen-containing heterocyclic derivative of the present invention may be added, if necessary, to the light emitting layer as long as the object of the present invention is not damaged. Further, a light emitting layer containing a different publicly known light emitting material may be laminated on the light emitting layer containing the nitrogen-containing heterocyclic derivative of the present invention.

The organic EL device of the present invention contains preferably at least one of an arylamine compound and a styrylamine compound in a light emitting layer.

The arylamine compound includes a compound represented by the following Formula (A), and the styrylamine compound includes a compound represented by the following Formula (B):

(A)

(in Formula (A), $Ar_8$ is a group selected from phenyl, biphenyl, terphenyl, stilbene and distyrylaryl; $Ar_9$ and $Ar_{10}$ each are a hydrogen atom or an aromatic group having 6 to 20 carbon atoms, and $Ar_9$ to $Ar_{10}$ may be substituted; p' is an integer of 1 to 4; and at least one of $Ar_9$ and $Ar_{10}$ is more preferably substituted with a styryl group).

In this regard, the aromatic group having 6 to 20 carbon atoms is preferably phenyl, naphthyl, anthranyl, phenanthryl, terphenyl or the like.

(B)

(in Formula (B), $Ar_{11}$ to $Ar_{13}$ are an aryl group having 5 to 40 ring carbon atoms which may be substituted, and q' is an integer of 1 to 4).

In this regard, the aryl group having 5 to 40 ring carbon atoms is preferably phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthenyl, acenaphthofluoranthenyl, stilbene and the like. The aryl group having 5 to 40 ring atoms may further be substituted with a substituent, and the preferred substituent includes an alkyl group having 1 to 6 carbon atoms (ethyl, methyl, isopropyl, n-propyl, s-butyl, t-butyl, pentyl, hexyl, cyclopentyl, cyclohexyl and the like), an alkoxy group having 1 to 6 carbon atoms (ethoxy, methoxy, isopropoxy, n-propoxy, s-butoxy, t-butoxy, pentoxy, hexyloxy, cyclopentoxy, cyclohexyloxy and the like), an aryl group having 5 to 40 ring atoms, an amino group substituted with an aryl group having 5 to 40 ring atoms, an ester group having an aryl group having 5 to 40 ring atoms, an ester group having an alkyl group having 1 to 6 carbon atoms, a cyano group, a nitro group and a halogen atom (chlorine, bromine, iodine and the like).

The light emitting material or the doping material includes, for example, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxynoid compounds, quinacridone, rubrene, fluorescent coloring matters and the like. However, it shall not be restricted to them.

The host material which can be used for the light emitting layer is preferably compounds represented by the following Formulas (i) to (ix).

Asymmetric anthracene represented by the following Formula (1):

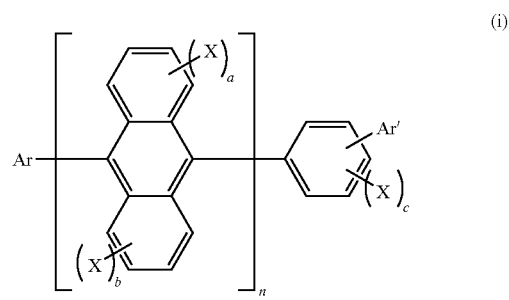

(i)

(wherein Ar is a substituted or non-substituted fused aromatic group having 10 to 50 ring carbon atoms;

Ar' is a substituted or non-substituted aromatic group having 6 to 50 ring carbon atoms;

X is a substituted or non-substituted aromatic group having 6 to 50 ring carbon atoms, a substituted or non-substituted aromatic heterocyclic group having 5 to 50 ring atoms, a substituted or non-substituted alkyl group having 1 to 50 carbon atoms, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a carboxyl group, a halogen atom, a cyano group, a nitro group or a hydroxyl group;

a, b and c each are an integer of 0 to 4;

n is an integer of 1 to 3; and when n is 2 or more, an inside of a parenthesis may be the same or different).

Asymmetric monoanthracene derivative represented by the following Formula (ii):

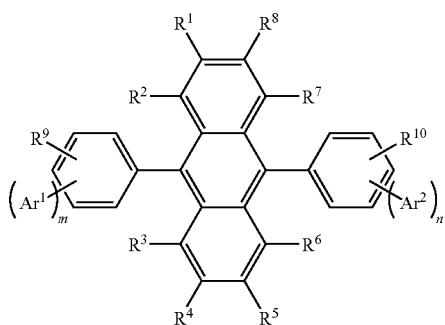

(ii)

(wherein $Ar^1$ and $Ar^2$ each are independently a substituted or non-substituted aromatic ring group having 6 to 50 ring carbon atoms; m and n each are an integer of 1 to 4; provided that when m and n are 1 and the positions of $Ar^1$ and $Ar^2$ bonded to the benzene ring are bilaterally symmetric, $Ar^1$ and $Ar^2$ are not the same, and when m and n are an integer of 2 to 4, m and n are different integers; and $R^1$ to $R^{10}$ each are independently a hydrogen atom, a substituted or non-substituted aromatic ring group having 6 to 50 ring carbon atoms, a substituted or non-substituted aromatic heterocyclic group having 5 to 50 ring atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group).

Asymmetric pyrene derivative represented by the following Formula (iii):

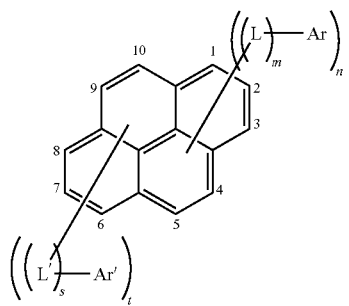

(iii)

(wherein Ar and Ar' each are a substituted or non-substituted aromatic group having 6 to 50 ring carbon atoms;

L and L' each are a substituted or non-substituted phenylene group, a substituted or non-substituted naphthalenylene group, a substituted or non-substituted fluorenylene group or a substituted or non-substituted dibenzosilolylene group;

m is an integer of 0 to 2; n is an integer of 1 to 4; s is an integer of 0 to 2; and t is an integer of 0 to 4;

L or Ar is bonded to any of 1- to 5-positions of pyrene, and L' or Ar' is bonded to any of 6- to 10-positions of pyrene; provided that when n+t is an even number, Ar, Ar', L and L' satisfy (1) or (2) described below:

(1) at least one of Ar≠Ar' and L≠L' (in this case, ≠ shows that both are groups having different structures) and (2) when Ar≠Ar' and L=L',
 (2-1) at least one of m≠s and n≠t or
 (2-2) when m≠s and n≠t,
  (2-2-1) L and L' or pyrene each are bonded to different bonding positions on Ar and Ar' or (2-2-2) when L and L' or pyrene are bonded to the same bonding position on Ar and Ar', there is not a case in which the substitution positions of L and L' or Ar and Ar' in pyrene are a 1-position and a 6-position or a 2-position and a 7-position).

Asymmetric anthracene derivative represented by the following Formula (iv):

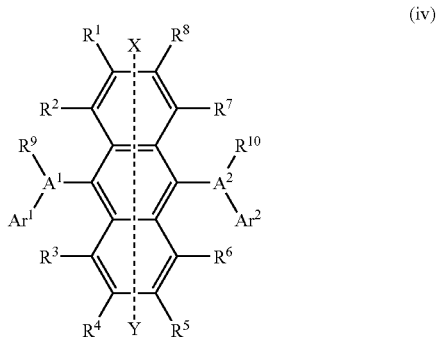

(iv)

(wherein $A^1$ and $A^2$ each are independently a substituted or non-substituted fused aromatic group having 10 to 20 ring carbon atoms;

$Ar^1$ and $Ar^2$ each are independently a hydrogen atom or a substituted or non-substituted aromatic ring group having 6 to 50 ring carbon atoms;

$R^1$ to $R^{10}$ each are independently a hydrogen atom, a substituted or non-substituted aromatic ring group having 6 to 50 ring carbon atoms, a substituted or non-substituted aromatic heterocyclic group having 5 to 50 ring atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group;

Ar$^1$, Ar$^2$, R$^9$ and R$^{10}$ each may be plural, and the adjacent groups may form a saturated or unsaturated cyclic structure; provided that there is no case in which in Formula (1), the groups symmetric to an X-Y axis shown on anthracene in a center are bonded to a 9-position and a 10-position of the above anthracene).

Anthracene derivative represented by the following Formula (v):

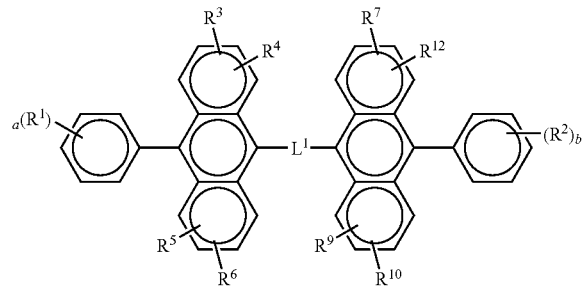

(v)

(wherein R$^1$ to R$^{10}$ each represent independently a hydrogen atom, an alkyl group, a cycloalkyl group, an aryl group which may be substituted, an alkoxyl group, an aryloxy group, an alkylamino group, an alkenyl group, an arylamino group or a heterocyclic group which may be substituted; a and b each represent an integer of 1 to 5; when they are 2 or more, R$^1$'s themselves or R$^2$'s themselves may be the same as or different from each other, and R$^1$'s themselves or R$^2$'s themselves may be combined with each other to form a ring; R$^3$ and R$^4$, R$^5$ and R$^6$, R$^7$ and R$^8$ and R$^9$ and R$^{10}$ may be combined with each other to form rings; and L$^1$ represents a single bond, —O—, —S—, —N(R)— (R is an alkyl group or an aryl group which may be substituted), an alkylene group or an arylene group).

Anthracene derivative represented by the following Formula (vi):

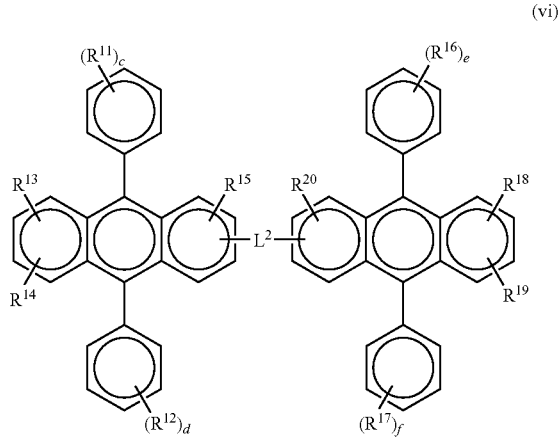

(vi)

(wherein R$^{11}$ to R$^{20}$ each represent independently a hydrogen atom, an alkyl group, a cycloalkyl group, an aryl group, an alkoxyl group, an aryloxy group, an alkylamino group, an arylamino group or a heterocyclic group which may be substituted; c, d, e and f each represent an integer of 1 to 5; when they are 2 or more, R$^{11}$'s themselves, R$^{12}$'s themselves, R$^{16}$'s themselves or R$^{17}$'s themselves may be the same as or different from each other, and R$^{11}$'s themselves, R$^{12}$'s themselves, R$^{16}$'s themselves or R$^{17}$'s themselves may be combined with each other to form a ring; a pair of R$^{13}$ and R$^{14}$, and a pair of R$^{18}$ and R$^{19}$ may be combined with each other to form rings; and L$^2$ represents a single bond, —O—, —S—, —N(R)— (R is an alkyl group or an aryl group which may be substituted), an alkylene group or an arylene group).

Spirofluorene derivative represented by the following Formula (vii):

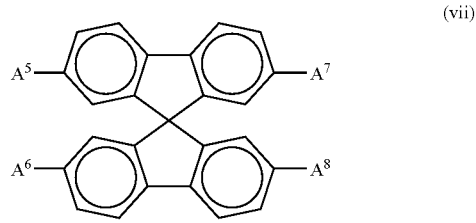

(vii)

(wherein A$^5$ to A$^8$ each are independently a substituted or non-substituted biphenyl group or a substituted or non-substituted naphthyl group).

Fused ring-containing compound represented by the following Formula (viii):

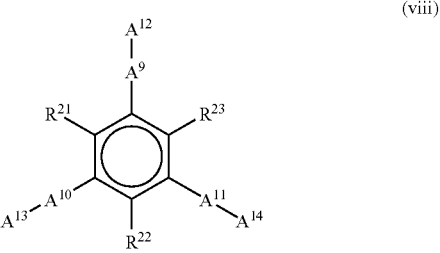

(viii)

(wherein A$^9$ to A$^{14}$ are the same as those described above; R$^{21}$ to R$^{23}$ each represent independently a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom; and at least one of A$^9$ to A$^{14}$ is a group having a fused aromatic rings having 3 or more rings).

Fluorene compound represented by the following Formula (1x):

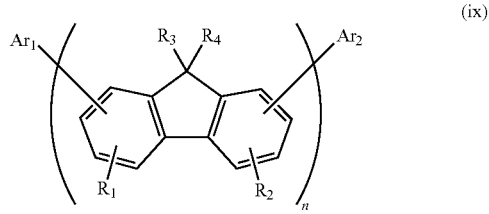

(ix)

(wherein $R_1$ and $R_2$ represent a hydrogen atom, a substituted or non-substituted alkyl group, a substituted or non-substituted aralkyl group, a substituted or non-substituted aryl group, a substituted or non-substituted heterocyclic group, a substituted amino group, a cyano group or a halogen atom; $R_1$'s themselves and $R_2$'s themselves which are bonded to the different fluorene groups may be the same as or different from each other, and $R_1$ and $R_2$ which are bonded to the same fluorene group may be the same or different; $R_3$ and $R_4$ represent a hydrogen atom, a substituted or non-substituted alkyl group, a substituted or non-substituted aralkyl group, a substituted or non-substituted aryl group or a substituted or non-substituted heterocyclic group; $R_3$'s themselves and $R_4$'s themselves which are bonded to the different fluorene groups may be the same as or different from each other, and $R_3$ and $R_4$ which are bonded to the same fluorene group may be the same or different; $Ar_1$ and $Ar_2$ represent a substituted or non-substituted fused polycyclic aromatic group in which the total of benzene rings is 3 or more or a fused polycyclic heterocyclic group in which the total of benzene rings and heterocycles is 3 or more and which is bonded to the fluorene group via substituted or non-substituted carbon; $Ar_1$ and $Ar_2$ may be the same or different; and n represents an integer of 1 to 10).

Among the host materials described above, the anthracene derivatives are preferred, and the monoanthracene derivative is more preferred. The asymmetric anthracene is particularly preferred.

Phosphorescent compounds can also be used as the light emitting material of a dopant. Compounds containing a carbazole ring for a host material are preferred as the phosphorescent compound. The dopant is a compound which can emit light from a triplet exciton, and it shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred.

The host suited to phosphorescence comprising the compound containing a carbazole ring is a compound having a function in which transfer of energy from an excited state thereof to a phosphorescent compound takes place to result in allowing the phosphorescent compound to emit light. The host compound shall not specifically be restricted as long as it is a compound which can transfer exciton energy to the phosphorescent compound, and it can suitably be selected according to the purposes. It may have an optional heterocycle in addition to a carbazole ring.

The specific examples of the above host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine derivatives, styrylamine derivatives, aromatic dimethylidene base compounds, porphyrin base compounds, anthraquinodimethane derivatives, anthrone derivatives, diphenylquinone derivatives, thiopyran dioxide derivatives, carbodiimide derivatives, fluorenilidenemethane derivatives, distyrylpyrazine derivatives, heterocyclic tetracarboxylic anhydride such as naphthaleneperylene and the like, phthalocyanine derivatives, metal complexes of 8-quinolinol derivatives and high molecular compounds including various metal complex polysilane base compounds represented by metal complexes comprising metal phthalocyanine, benzoxazole and benzothiazole as ligands, poly(N-vinylcarbazole) derivatives, aniline base copolymers, thiophene oligomers, electroconductive high molecular oligomers such as polythiophene, polythiophene derivatives, polyphenylene derivatives, polyphenylenevinylene derivatives and polyfluorene derivatives. The host compounds may be used alone or in combination of two or more kinds thereof.

The specific examples thereof include the following compounds:

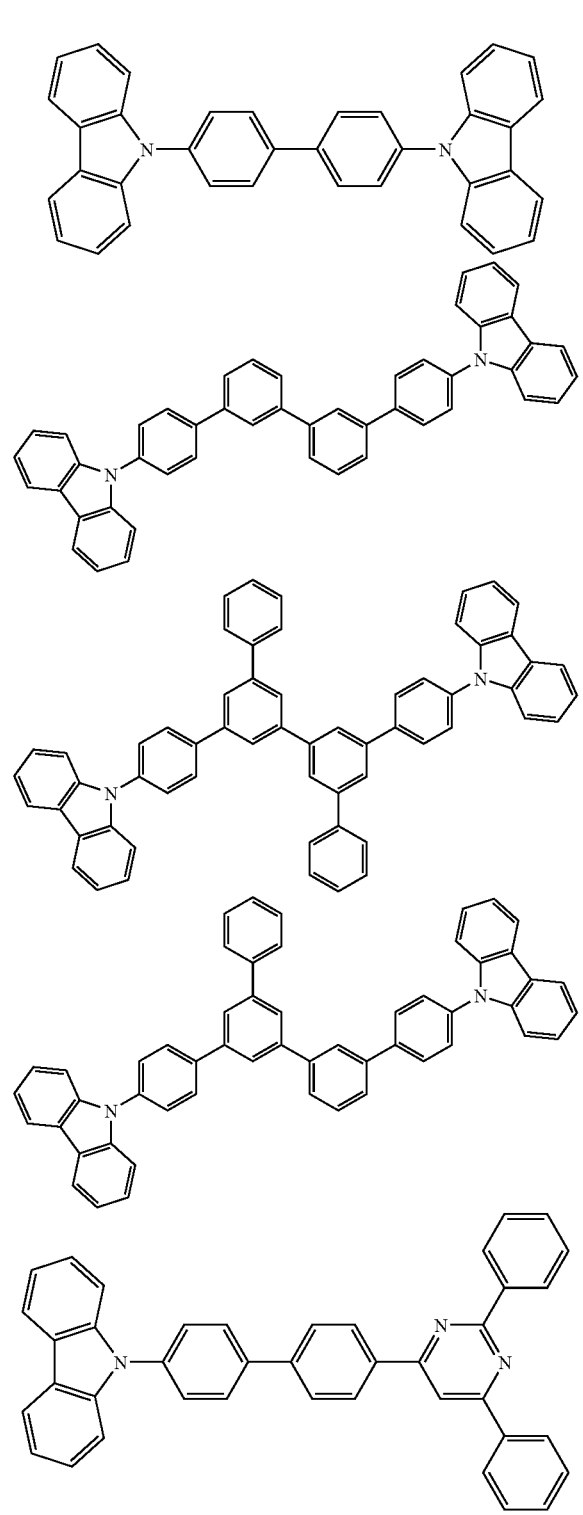

-continued

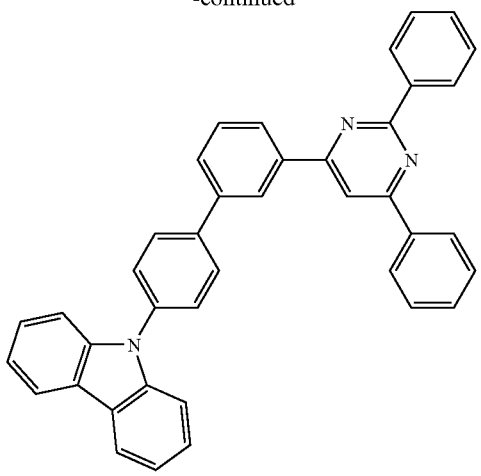

The phosphorescent dopant is a compound which can emit light from a triplet exciton. It shall not specifically be restricted as long as light is emitted from a triplet exciton. It is preferably a metal complex containing at least one metal selected from the group consisting of Ir, Ru, Pd, Pt, Os and Re, and a porphyrin metal complex or an ortho-metallated metal complex is preferred. The porphyrin metal complex is preferably a porphyrin platinum complex. The phosphorescent compounds may be used alone or in combination of two or more kinds thereof.

A ligand forming the ortho-metallated metal complex includes various ones, and the preferred ligand includes 2-phenylpyridine derivatives, 7,8-benzoquinoline derivatives, 2-(2-thienyl)pyridine derivatives, 2-(1-naphthyl)pyridine derivatives, 2-phenylquinoline derivatives and the like. The above derivatives may have, if necessary, substituents. In particular, the compounds into which fluorides and trifluoromethyl are introduced are preferred as a blue color dopant. Further, it may have, as an auxiliary ligand, ligands other than the ligands described above such as acetylacetonate, picric acid and the like.

A content of the phosphorescent dopant in the light emitting layer shall not specifically be restricted, and it can suitably be selected according to the purposes. It is, for example, 0.1 to 70 mass %, preferably 1 to 30 mass %. If a content of the phosphorescent dopant is less than 0.1 mass %, light emission is faint, and an addition effect thereof is not sufficiently exhibited. On the other hand, if it exceeds 70 mass %, a phenomenon called concentration quenching is markedly brought about, and the device performance is reduced.

The light emitting layer may contain, if necessary, a hole transporting material, an electron transporting material and a polymer binder.

Further, a film thickness of the light emitting layer is preferably 5 to 50 nm, more preferably 7 to 50 nm and most preferably 10 to 50 nm. If it is less than 5 nm, it is difficult to form the light emitting layer, and controlling of the chromaticity is likely to become difficult. On the other hand, if it exceeds 50 nm, the operating voltage is likely to go up.

(5) Hole Injecting and Transporting Layer (Hole Transporting Zone)

The hole injecting and transporting layer is a layer for assisting injection of a hole into the light emitting layer to transport it to the light emitting region, and it has a large hole mobility and shows a small ionization energy of usually 5.5 eV or less. A material which transports a hole to the light emitting layer by a lower electric field strength is preferred as the above hole injecting and transporting layer, and more preferred is a material in which a mobility of a hole is at least $10^{-4}$ cm$^2$/V·second in applying an electric field of, for example, $10^4$ to $10^6$ V/cm.

The materials for forming the hole injecting and transporting layer in the organic EL device of the present invention shall not specifically be restricted as long as they have the preferred properties described above, and capable of being used are optional materials selected from materials which have so far conventionally been used as charge transporting materials for holes in photoconductive materials and publicly known materials which are used for a hole injecting and transporting layer in an organic EL device.

The specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No. 16096/1962 and the like), polyarylalkane derivatives (refer to U.S. Pat. No. 3,615,402, ditto U.S. Pat. No. 3,820,989 and ditto U.S. Pat. No. 3,542,544, Japanese Patent Publication No. 555/1970 and ditto No. 10983/1976 and Japanese Patent Application Laid-Open No. 93224/1976, ditto No. 17105/1980, ditto No. 4148/1981, ditto No. 108667/1980, ditto No. 156953/1980 and ditto No. 36656/1981 and the like), pyrazoline derivatives and pyrazolone derivatives (refer to U.S. Pat. No. 3,180,729 and ditto U.S. Pat. No. 4,278,746 and Japanese Patent Application Laid-Open No. 88064/1980, ditto No. 88065/1980, ditto No. 105537/1974, ditto No. 51086/1980, ditto No. 80051/1981, ditto No. 88141/1981, ditto No. 45545/1982, ditto No. 112637/1979 and ditto No. 74546/1980 and the like), phenylenediamine derivatives (refer to U.S. Pat. No. 3,615,404, Japanese Patent Publication No. 10105/1976, ditto No. 3712/1971 and ditto No. 25336/1972 and Japanese Patent Application Laid-Open No. 53435/1979, ditto No. 110536/1979 and ditto No. 119925/1979 and the like), arylamine derivatives (refer to U.S. Pat. No. 3,567,450, ditto U.S. Pat. No. 3,180,703, ditto U.S. Pat. No. 3,240,597, ditto U.S. Pat. No. 3,658,520, ditto U.S. Pat. No. 4,232,103, ditto U.S. Pat. No. 4,175,961 and ditto U.S. Pat. No. 4,012,376, Japanese Patent Publication No. 35702/1974 and ditto No. 27577/1964, Japanese Patent Application Laid-Open No. 144250/1980, ditto No. 119132/1981 and ditto No. 22437/1981 and German Patent No. 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-Open No. 46234/1981 and the like), fluorenone derivatives (refer to Japanese Patent Application Laid-Open No. 110837/1979 and the like), hydrazone derivatives (refer to U.S. Pat. No. 3,717,462, Japanese Patent Application Laid-Open No. 59143/1979, ditto No. 52063/1980, ditto No. 52064/1980, ditto No. 46760/1980, ditto No. 85495/1980, ditto No. 11350/1982 and ditto No. 148749/1982, Japanese Patent Application Laid-Open No. 311591/1990 and the like), stilbene derivatives (Japanese Patent Application Laid-Open No. 210363/1986, ditto No. 228451/1986, ditto No. 14642/1986, ditto No. 72255/1986, ditto No. 47646/1987, ditto No. 36674/1987, ditto No. 10652/1987, ditto No. 30255/1987, ditto No. 93455/1985, ditto No. 94462/1985, ditto No. 174749/1985 and ditto No. 175052/1985 and the like), silazane derivatives (U.S. Pat. No. 4,950,950), polysilane base (Japanese Patent Application Laid-Open No. 204996/1990), aniline base copolymers (Japanese Patent Application Laid-Open No. 282263/1990), electroconductive high molecular oligomers (particularly thiophene oligomers) disclosed in Japanese Patent Application Laid-Open No. 211399/1989, and the like.

The compounds described above can be used as the material for the hole injecting and transporting layer, and preferably used are porphyrin compounds (disclosed in Japanese Patent Application Laid-Open No. 2956965/1988 and the like), aromatic tertiary amine compounds and styrylamine compounds (refer to U.S. Pat. No. 4,127,412 and Japanese Patent Application Laid-Open No. 27033/1978, ditto No. 58445/1979, ditto No. 149634/1979, ditto No. 64299/1979, ditto No. 79450/1980, ditto No. 144250/1980, ditto No. 119132/1981, ditto No. 295558/1986, ditto No. 98353/1986 and ditto No. 295695/1988 and the like), and the aromatic tertiary amine compounds are particularly preferably used.

Further, capable of being given are compounds having two fused aromatic rings in a molecule described in U.S. Pat. No. 5,061,569, for example, 4,4'-bis(N-(1-naphthyl)-N-phenylamino)biphenyl (hereinafter abbreviated as NPD) and 4,4',4''-tris(N-(3-methylphenyl)-N-phenylamino)triphenylamine (hereinafter abbreviated as MTDATA) in which three triphenylamine units are combined in the form of a star burst type described in Japanese Patent Application Laid-Open No. 308688/1992.

Further, inorganic compounds such as p type Si, p type SiC and the like can also be used as the material for the hole injecting and transporting layer in addition to the aromatic dimethylidene base compounds described above shown as the material for the light emitting layer.

The hole injecting and transporting layer can be formed by making a thin film from the hole injecting and transporting material described above by a publicly known method such as, for example, a vacuum vapor deposition method, a spin coating method, a casting method, an LB method and the like. A film thickness of the hole injecting and transporting layer shall not specifically be restricted, and it is usually 5 nm to 5 μm. The above hole injecting and transporting layer may be constituted from a single layer comprising at least one of the materials described above as long as the hole injecting and transporting material described above is contained in the hole transporting zone, and a hole injecting and transporting layer comprising a compound which is different from the compound used in the hole injecting and transporting layer described above may be laminated thereon.

Further, an organic semiconductor layer may be provided as a layer for assisting injection of a hole or injection of an electron into the light emitting layer, and the layer having a conductance of $10^{-10}$ S/cm or more is suited. Capable of being used as a material for the above organic semiconductor layer are conductive oligomers such as thiophene-containing oligomers and arylamine-containing oligomers disclosed in Japanese Patent Application Laid-Open No. 193191/1996 and conductive dendrimers such as arylamine-containing dendrimers.

(6) Electron Injecting and Transporting Layer

The electron injecting and transporting layer of the present invention is a layer assisting injection of an electron into the light emitting layer to transport it to the light emitting region, and it has a large electron mobility. Also, the adhesion improving layer is a layer comprising particularly a material having a good adhesive property with the cathode in the above electron injecting layer. In the organic EL device of the present invention, the foregoing compound of the present invention is used preferably for the electron injecting and transporting layer and the adhesion improving layer.

When the nitrogen-containing heterocyclic derivative of the present invention is used in the electron transporting zone, the electron injecting and transporting layer may be formed from the nitrogen-containing heterocyclic derivative of the present invention alone or it may be used in a mixture or a laminate with other materials.

The materials for forming the electron injecting and transporting layer by mixing or laminating with the nitrogen-containing heterocyclic derivative of the present invention shall not specifically be restricted as long as they have the preferred properties described above, and capable of being used are optional materials selected from materials which have so far conventionally been used as charge transporting materials for electrons in photoconductive materials and publicly known materials which are used for an electron injecting and transporting layer in an organic EL device.

The preferred mode of the organic EL device of the present invention includes a device containing a reducing dopant in the region which transports an electron or an interfacial region between the cathode and the organic layer. In the present invention, preferred is the organic EL device in which a reducing dopant is contained in the compound of the present invention. In this case, the reducing dopant is defined by a substance which can reduce an electron transporting compound. Accordingly, various compounds can be used as long as they have a certain reducing property, and capable of being suitably used is at least one substance selected from the group consisting of, for example, alkali metals, alkaline earth metals, rare earth metals, oxides of alkali metals, halides of alkali metals, oxides of alkaline earth metals, halides of alkaline earth metals, oxides of rare earth metals or halides of rare earth metals, organic complexes of alkali metals, organic complexes of alkaline earth metals and organic complexes of rare earth metals.

To be more specific, the preferred reducing dopant includes at least one alkali metal selected from the group consisting of Na (work function: 2.36 eV), K (work function: 2.28 eV), Rb (work function: 2.16 eV) and Cs (work function: 1.95 eV) and at least one alkaline earth metal selected from the group consisting of Ca (work function: 2.9 eV), Sr (work function: 2.0 to 2.5 eV) and Ba (work function: 2.52 eV), and the compounds having a work function of 2.9 eV or less are particularly preferred. Among them, the preferred reducing dopant is at least one alkali metal selected from the group consisting of K, Rb and Cs, the more preferred reducing dopant is Rb or Cs, and the most preferred reducing dopant is Cs. The above alkali metals have a particularly high reducing ability, and addition of a relatively small amount thereof to the electron injecting zone makes it possible to raise a light emitting luminance in the organic EL device and extend a lifetime thereof. The combination of two or more kinds of the above alkali metals is preferred as the reducing dopant having a work function of 2.9 eV or less, and particularly preferred is the combination containing Cs, for example, the combination of Cs with Na, Cs with K, Cs with Rb or Cs with Na and K. Containing Cs in combination makes it possible to efficiently exhibit the reducing ability, and addition thereof to the electron injecting zone makes it possible to enhance a light emitting luminance in the organic EL device and extend a lifetime thereof.

In the present invention, an electron injecting layer constituted from an insulator or a semiconductor may further be provided between the cathode and the organic layer. In this case, an electric current can effectively be prevented from leaking to enhance the electron injecting property. Preferably used as the above insulator is at least one metal compound selected from the group consisting of alkali metal chalcogenides, alkaline earth metal chalcogenides, halides of alkali metals and halides of alkaline earth metals. If the electron injecting layer is constituted from the above alkali metal chalcogenides and the like, it is preferred from the viewpoint that the electron injecting property can further be enhanced. To be specific, the preferred alkali metal chalcogenides include, for example, $Li_2O$, $K_2O$, $Na_2S$, $Na_2Se$ and $Na_2O$, and the preferred alkaline earth metal chalcogenides include, for example, CaO, BaO, SrO, BeO, BaS and CaSe. Also, the preferred halides of alkali metals include, for example, LiF, NaF, KF, LiCl, KCl and NaCl. Further, the preferred halides of alkaline earth metals include, for example, fluorides such as $CaF_2$, $BaF_2$, $SrF_2$, $MgF_2$ and $BeF_2$ and halides other than the fluorides.

The semiconductor constituting the electron transporting layer includes a single kind of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron transporting layer is preferably a microcrystalline or amorphous insulating thin film. If the electron transporting layer is constituted from the above insulating thin film, the more homogeneous thin film is formed, and therefore picture element defects such as dark spots and the like can be reduced. The above inorganic compound includes the alkali metal chalcogenides, the alkaline earth metal chalcogenides, the halides of alkali metals and the halides of alkaline earth metals each described above.

(7) Cathode

Cathodes prepared by using metals, alloys, electroconductive compounds and mixtures thereof each having a small work function (4 eV or less) for electrode materials are used as the cathode in order to inject electrons into the electron injecting and transporting layer or the light emitting layer. The specific examples of the above electrode materials include sodium, sodium.potassium alloys, magnesium, lithium, magnesium.silver alloys, aluminum/aluminum oxide, aluminum.lithium alloys, indium, rare earth metals and the like.

The above cathode can be prepared by forming a thin film from the above electrode materials by a method such as vapor deposition, sputtering and the like.

In this respect, when light emitted from the light emitting layer is taken out from the cathode, a transmittance of the cathode based on light emitted is preferably larger than 10%.

A sheet resistance of the cathode is preferably several hundred Ω/square or less, and a film thickness thereof is usually 10 nm to 1 μm, preferably 50 to 200 nm.

(8) Insulating Layer

The organic EL device is liable to cause picture element defects by leak and short since an electric field is applied to an ultrathin film. In order to prevent the above matter, an insulating thin film layer is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like, and mixtures and laminates thereof may be used as well.

(9) Production Process for Organic EL Device

According to the materials and the forming methods which have been shown above as the examples, the anode, the light emitting layer, if necessary, the hole injecting and transporting layer and, if necessary, the electron injecting and transporting layer are formed, and further the cathode is formed, whereby the organic EL device can be prepared. Also, the organic EL device can be prepared as well in an order of from the cathode to the anode which is reverse to the order described above.

A preparation example of an organic EL device having a constitution in which an anode/a hole injecting layer/a light emitting layer/an electron injecting layer/a cathode are provided in order on a light transmitting substrate shall be described below.

First, a thin film comprising an anode material is formed on a suitable light transmitting substrate by a method such as vapor deposition, sputtering and the like so that a film thickness falling in a range of 1 μm or less, preferably 10 to 200 nm is obtained, whereby an anode is prepared. Next, a hole injecting layer is provided on the above anode. The hole injecting layer can be formed, as described above, by a method such as a vacuum vapor deposition method, a spin coating method, a casting method, an LB method and the like, and it is formed preferably by the vacuum vapor deposition method because of the reasons that the homogeneous film is liable to be obtained and that pinholes are less liable to be produced. When forming the hole injecting layer by the vacuum vapor deposition method, the depositing conditions thereof are varied according to the compounds used (the materials for the hole injecting layer), the crystal structure of the targeted hole injecting layer and the recombination structure thereof, and in general, they are suitably selected preferably in the ranges of a deposition source temperature of 50 to 450° C., a vacuum degree of $10^{-7}$ to $10^{-3}$ Torr, a depositing speed of 0.01 to 50 nm/second, a substrate temperature of −50 to 300° C. and a film thickness of 5 nm to 5 μm.

Next, a light emitting layer can be formed on the hole injecting layer by forming a thin film from the desired organic light emitting material by a method such as a vacuum vapor deposition method, sputtering, a spin coating method, a casting method and the like, and it is formed preferably by the vacuum vapor deposition method because of the reasons that the homogeneous film is liable to be obtained and that pinholes are less liable to be produced. When forming the light emitting layer by the vacuum vapor deposition method, the depositing conditions thereof are varied according to the compounds used, and in general, they can be selected from the same condition ranges as in the hole injecting layer.

Next, an electron injecting layer is provided on the above light emitting layer. It is formed preferably by the vacuum vapor deposition method as is the case with the hole injecting layer and the light emitting layer since the homogeneous film has to be obtained. The depositing conditions thereof can be selected from the same condition ranges as in the hole injecting layer and the light emitting layer.

When using the vacuum vapor deposition method, the nitrogen-containing heterocyclic derivative of the present invention can be codeposited together with the other materials, though varied depending on that it is added to any layer in the light emitting zone, the electron injecting zone or the electron transporting zone. When using the spin coating method, it can be added in a mixture with the other materials.

Lastly, a cathode is laminated, whereby an organic EL device can be obtained.

The cathode is constituted from metal, and therefore the vapor deposition method and the sputtering method can be used. However, the vacuum vapor deposition method is preferred in order to protect the organic substance layer of the base from being damaged in making the film.

The above organic EL device is preferably prepared serially from the anode up to the cathode in one vacuuming.

The forming methods of the respective layers in the organic EL device of the present invention shall not specifically be restricted, and forming methods carried out by a vacuum vapor deposition method, a spin coating method and the like which have so far publicly been known can be used. The organic thin film layer containing the compound represented by Formula (1) described above which is used for the organic EL device of the present invention can be formed by a publicly known method carried out by a vacuum vapor deposition method, a molecular beam evaporation method (MBE method) and a coating method such as a dipping method, a spin coating method, a casting method, a bar coating method and a roll coating method each using a solution prepared by dissolving the compound in a solvent.

The film thicknesses of the respective organic layers in the organic EL device of the present invention shall not specifically be restricted, and in general, if the film thicknesses are too small, defects such as pinholes and the like are liable to be caused. On the other hand, if they are too large, high voltage has to be applied, and the efficiency is deteriorated, so that they fall usually in a range of preferably several nm to 1 μm.

When applying a DC voltage to the organic EL device, light emission can be observed by applying a voltage of 5 to 40 V setting a polarity of the anode to plus and that of the cathode to minus. An electric current does not flow by applying a voltage at a reverse polarity, and light emission is not caused at all. Further, when applying an AC voltage, uniform light emission can be observed only in a case where the anode has a plus polarity and where the cathode has a minus polarity. A waveform of an alternating current applied may be arbitrary.

EXAMPLES

Next, the present invention shall be explained in further details with reference to examples, but the present invention shall by no means be restricted by these examples.

Synthetic Example 1

(1-1) Synthesis of Intermediate 1

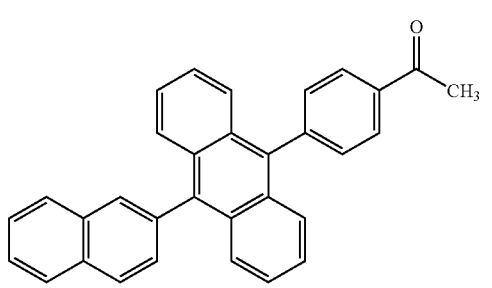

Intermediate 1

A 500 mL three neck flask was charged with 4.8 g (24 mmol) of 4-bromoacetophenone, 10 g (29 mmol) of 10-naphthalene-2-yl-anthracene-9-boronic acid, 0.55 g (0.5 mmol) of tetrakistriphenylphosphinepalladium (0), 100 mL of 1,2-dimethoxyethane and 45 mL of a 2M sodium carbonate aqueous solution under argon flow, and the mixture was heated and refluxed for 8 hours. After finishing the reaction, the organic layer was washed with water and dried on magnesium sulfate, and the solvent was removed by distillation by means of a rotary evaporator. The resulting crude crystal was recrystallized from ethanol to obtain 8.5 g (white crystal, yield: 70%) of the targeted intermediate 1.

(1-2) Synthesis of Compound (1)

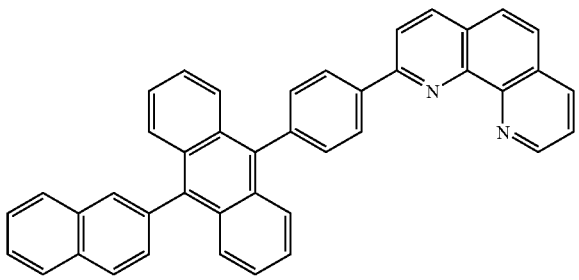

Compound (1)

The intermediate 1 4.0 g (9.5 mmol), 8-aminoquinoline-7-carboaldehyde 1.7 g (9.9 mmol) and ethanol 40 mL were added and dissolved by heating under argon atmosphere. A saturated potassium hydroxide ethanol solution 10 mL was dropwise added to the above solution, and the mixture was heated and refluxed for 9 hours. After left cooling down to room temperature, the resulting solid matter was obtained by filtration and washed with ethanol, and then it was dried under reduced pressure to obtain a crude reaction product. It was refined by column chromatography (silica gel dichloromethane:hexane) to obtain 3.7 g (white crystal, yield: 70%) of the targeted compound (1). This product was measured by FD-MS (field desorption mass spectrum), whereby it was identified as the compound (1).

Synthetic Example 2

(2-1) Synthesis of Intermediate 2

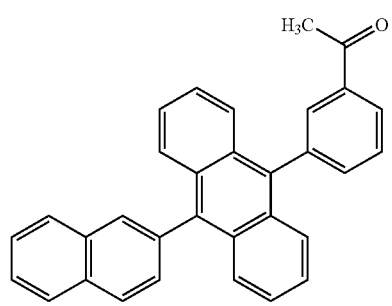

Intermediate 2

An intermediate 2 was obtained by carrying out the same operation, except that in Synthetic Example 1 (1-1), 3-bromoacetophenone was used in place of 4-bromoacetophenone. Yield: 60%.

(2-2) Synthesis of Compound (2)

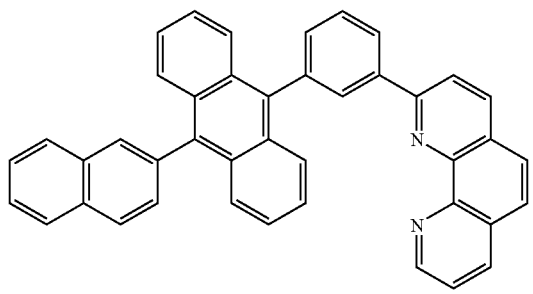

Compound (2)

A compound (2) was obtained by carrying out the same operation, except that in Synthetic Example 2 (1-2), the intermediate 2 was used in place of the intermediate 1. This product was measured by FD-MS (field desorption mass spectrum), whereby it was identified as the compound (2). Yield: 50%.

Example 1

Production of Organic EL Device in which the Compound of the Present Invention is Used in an Electron Injecting Layer A glass substrate (manufactured by Geomatech Co., Ltd.) of 25 mm×75 mm×1.1 mm thickness equipped with an ITO transparent electrode (anode) was subjected to supersonic wave washing in isopropyl alcohol for 5 minutes and then to UV ozone washing for 30 minutes. After washed, the glass substrate equipped with an ITO transparent electrode line was loaded in a substrate holder of a vacuum vapor deposition apparatus, and a N,N'-bis(N,N'-diphenyl-4-aminophenyl)-N, N-diphenyl-4,4'-diamino-1,1'-biphenyl film (hereinafter abbreviated as a "TPD232 film") having a film thickness of 60 nm was first formed on a face of a side at which the transparent electrode line was formed so that it covers the transparent electrode described above. This TPD232 film functions as a hole injecting layer. After forming the TPD232 film, a 4,4'-bis[N-(1-naphthyl)-N-phenylamino]biphenyl film (hereinafter abbreviated as a "NPD film") having a film thickness of 20 nm was formed on the above TPD232 film. This NPD film functions as a hole transporting layer.

Further, a film of an anthracene derivative A1 shown below and a styrylamine derivative S1 shown below was formed in a film thickness of 40 nm at a film thickness ratio of 40:2 on the above NPD film to prepare a blue light emitting layer.

A film of the compound (1) was formed as an electron transporting layer in a film thickness of 20 nm on the above film by vapor deposition. Then, a film of LiF was formed thereon in a film thickness of 1 nm. Metal Al was deposited on the above LiF film in a film thickness of 150 nm to form a metal cathode, whereby an organic EL device was prepared.

A1

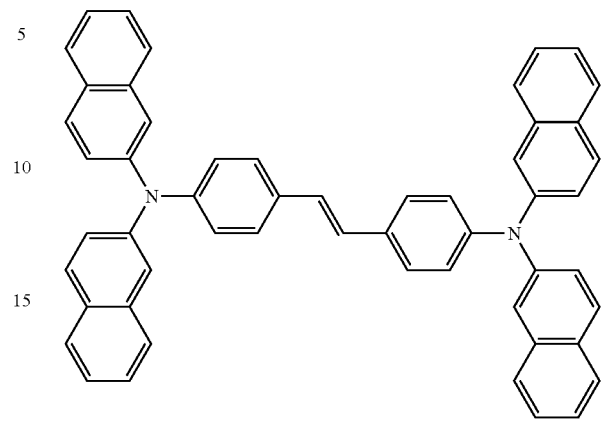

S1

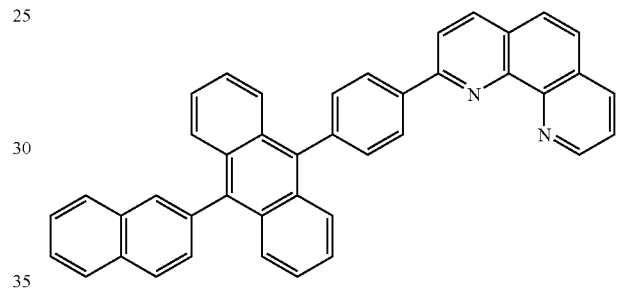

Compound (1)

Example 2

An organic EL device was prepared in the same manner, except that in Example 1, the compound (2) was used in place of the compound (1).

Compound (2)

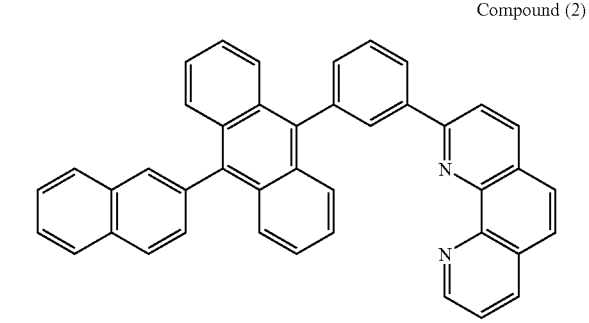

Comparative Example 1

An organic EL device was prepared in the same manner, except that in Example 1, the following compound A described in International Publication WO04/080975 was used in place of the compound (1).

Compound A

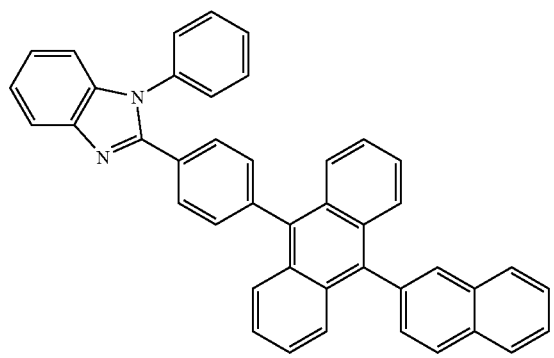

Comparative Example 2

An organic EL device was prepared in the same manner, except that in Example 1, the following compound B described in International Publication WO04/080975 was used in place of the compound (1).

Compound B

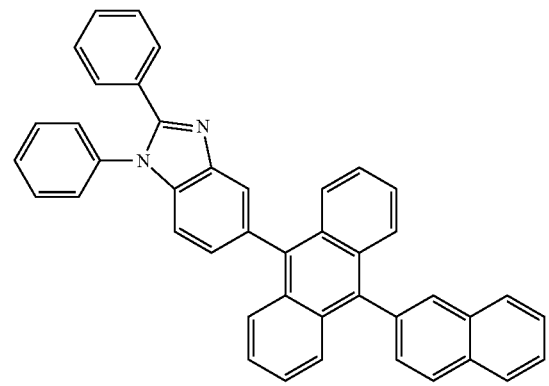

Comparative Example 3

An organic EL device was prepared in the same manner, except that in Example 1, Alq (aluminum complex of 8-hydroxyquinoline) was used in place of the compound (1).

Comparative Example 4

An organic EL device was prepared in the same manner, except that in Example 1, BCP (bathocuproine) was used in place of the compound (1).

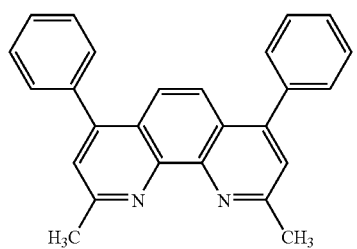

BCP

Evaluation of Organic EL Devices:

The light emitting luminances and the current efficiencies of the organic EL devices obtained in Examples 1 to 2 and Comparative Examples 1 to 4 were measured on a condition of applying DC voltages described in Table 1 shown below, and the light emitting colors thereof were observed. The results thereof are shown in Table 1.

TABLE 1

| | Compound in electron injecting layer | Voltage (V) | Current density (mA/cm$^2$) | Light emitting luminance (cd/m$^2$) | Current efficiency (cd/A) | Light emitting color |
|---|---|---|---|---|---|---|
| Example 1 | Compound (1) | 4.8 | 10.0 | 855.9 | 8.60 | Blue |
| Example 2 | Compound (2) | 5.0 | 10.0 | 817.2 | 8.17 | Blue |
| Comparative Example 1 | Compound A | 6.1 | 10.0 | 622.9 | 6.23 | Blue |
| Comparative Example 2 | Compound B | 5.3 | 10.0 | 740.0 | 7.40 | Blue |
| Comparative Example 3 | Alq | 6.2 | 10.0 | 480.3 | 4.80 | Blue |
| Comparative Example 4 | BCP | 5.6 | 10.0 | 671.7 | 6.72 | Blue |

It can be found from the results shown in Table 1 that use of the compounds described above in the electron injecting layer makes it possible to produce the organic EL devices having a very high light emitting luminance and current efficiency.

INDUSTRIAL APPLICABILITY

As explained above in details, the organic EL devices prepared by using the nitrogen-containing heterocyclic derivatives of the present invention provide blue light emission having a high light emitting luminance and a high current efficiency. Accordingly, they are useful as an organic EL device having a high practicality.

The invention claimed is:

1. A nitrogen-containing heterocyclic derivative represented by Formula (1):

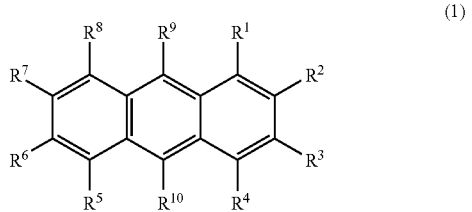

(1)

wherein in Formula (1), $R^1$ to $R^{10}$ each are independently a hydrogen atom, a substituted or non-substituted aryl group having 5 to 60 ring atoms, a pyridyl group which may have a substituent, a quinolyl group which may have a substituent, a substituted or non-substituted alkyl group having 1 to 50 carbon atoms, a substituted or non-substituted cycloalkyl group having 3 to 50 carbon atoms, a substituted or non-substituted aralkyl group having 6 to 50 ring atoms, a substituted or non-substituted alkoxy group having 1 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group;

a pair of the adjacent substituents in $R^1$ to $R^{10}$ may be combined with each other to form an aromatic ring; and at least one of $R^1$ to $R^{10}$ is a substituent represented by Formula (2):

(2)

wherein in Formula (2), L is an arylene group having 6 to 60 carbon atoms which may have a substituent, a pyridinylene group which may have a substituent, a quinolinylene group which may have a substituent or a fluorenylene group which may have a substituent; and HAr is a substituent formed by removing any one of $R^{1a}$ to $R^{8a}$ in a structure represented by Formula (3):

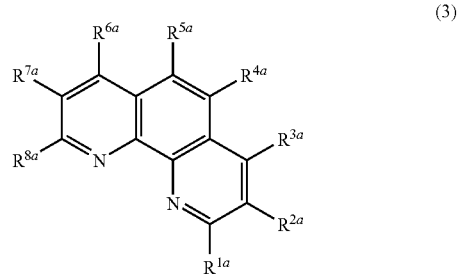

(3)

wherein in Formula (3), $R^{1a}$ to $R^{8a}$ each are independently a hydrogen atom, a substituted or non-substituted aryl group having 5 to 60 ring atoms, a pyridyl group which may have a substituent, a quinolyl group which may have a substituent, a substituted or non-substituted alkyl group having 1 to 50 carbon atoms, a substituted or non-substituted cycloalkyl group having 3 to 50 carbon atoms, a substituted or non-substituted aralkyl group having 6 to 50 ring atoms, a substituted or non-substituted alkoxy group having 1 to 50 carbon atoms, a substituted or non-substituted aryloxy group having 5 to 50 ring atoms, a substituted or non-substituted arylthio group having 5 to 50 ring atoms, a substituted or non-substituted alkoxycarbonyl group having 1 to 50 carbon atoms, an amino group substituted with a substituted or non-substituted aryl group having 5 to 50 ring atoms, a halogen atom, a cyano group, a nitro group, a hydroxyl group or a carboxyl group; and a pair of the adjacent substituents in $R^{1a}$ to $R^{8a}$ may be combined with each other to form an aromatic ring.

2. The nitrogen-containing heterocyclic derivative as claimed in claim 1, wherein the compound represented by Formula (1) is represented by the following Formula (1-a), (1-b), (1-c) or (1-d):

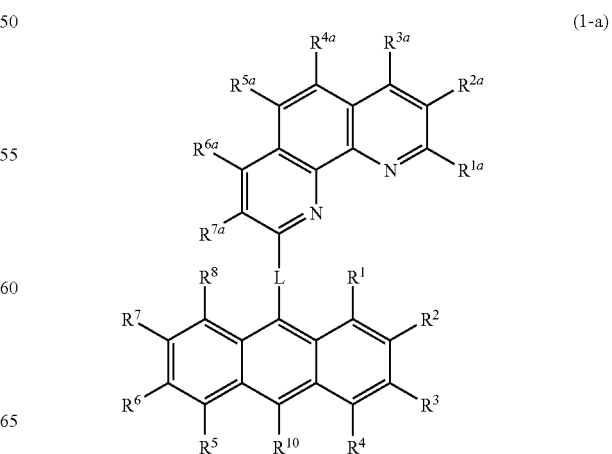

(1-a)

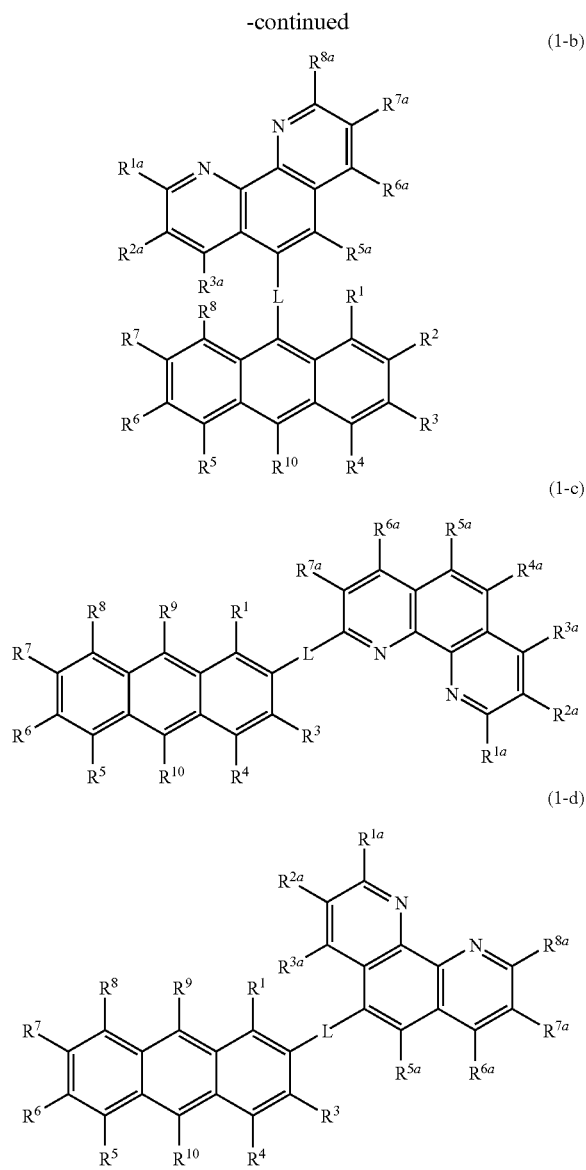

wherein $R^1$ to $R^{10}$ are the same as the groups in Formula (1); $R^{1a}$ to $R^{8a}$ are the same as the groups in Formula (3); and L is the same as the group in Formula (2).

3. The nitrogen-containing heterocyclic derivative as claimed in claim 1, wherein it is a material for an organic electroluminescence device.

4. The nitrogen-containing heterocyclic derivative as claimed in claim 1, wherein it is an electron injecting material or an electron transporting material for an organic electroluminescence device.

5. The nitrogen-containing heterocyclic derivative as claimed in claim 1, wherein it is a light emitting material for an organic electroluminescence device.

6. An organic electroluminescence device in which an organic thin film layer comprising a single layer or plural layers including at least a light emitting layer is interposed between a cathode and an anode, wherein at least one layer in the organic thin film layer contains the nitrogen-containing heterocyclic derivative as claimed in claim 1 in the form of a single component or a mixed component.

7. An organic electroluminescence device in which an organic thin film layer comprising a single layer or plural layers including at least a light emitting layer is interposed between a cathode and an anode, wherein the organic thin film layer comprises an electron injecting layer or an electron transporting layer, and the electron injecting layer or electron transporting layer contains the nitrogen-containing heterocyclic derivative as claimed in claim 1 in the form of a single component or a mixed component.

8. An organic electroluminescence device in which an organic thin film layer comprising a single layer or plural layers including at least a light emitting layer is interposed between a cathode and an anode, wherein the light emitting layer contains the nitrogen-containing heterocyclic derivative as claimed in claim 1 in the form of a single component or a mixed component.

9. An organic electroluminescence device in which an organic thin film layer comprising a single layer or plural layers including at least a light emitting layer is interposed between a cathode and an anode, wherein the organic thin film layer comprises an electron injecting layer or an electron transporting layer, and, wherein the electron injecting layer or electron transporting layer containing the nitrogen-containing heterocyclic derivative as claimed in claim 1 also contains a reducing dopant.

10. The organic electroluminescence device as claimed in claim 9, wherein the reducing dopant is at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals.

* * * * *